United States Patent [19]
Dunn et al.

[11] Patent Number: 5,717,030
[45] Date of Patent: Feb. 10, 1998

[54] ADJUNCTIVE POLYMER SYSTEM FOR USE WITH MEDICAL DEVICE

[75] Inventors: Richard L. Dunn; Gerald L. Yewey; Jeffrey L. Southard; John E. Urheim, all of Fort Collins, Colo.

[73] Assignee: Atrix Laboratories, Inc., Fort Collins, Colo.

[21] Appl. No.: 761,522

[22] Filed: Dec. 6, 1996

Related U.S. Application Data

[60] Continuation of Ser. No. 475,097, Jun. 7, 1995, which is a division of Ser. No. 226,006, Apr. 8, 1994.

[51] Int. Cl.$^6$ .................................................. A61L 15/12
[52] U.S. Cl. .................. 523/111; 523/113; 424/78.06; 424/426; 424/447; 602/52; 602/904; 528/905
[58] Field of Search ..................... 528/905; 523/111, 523/113; 424/78.06, 426, 447; 602/52, 904

[56] References Cited

U.S. PATENT DOCUMENTS

| | | | |
|---|---|---|---|
| 2,155,658 | 4/1939 | Herrmann | 424/426 |
| 3,463,158 | 8/1969 | Schmitt et al. | 128/334 |
| 3,773,919 | 11/1973 | Boswell et al. | 424/19 |
| 3,887,699 | 6/1975 | Yolles | 424/9 |
| 3,991,766 | 11/1976 | Schmitt et al. | 128/335.5 |
| 4,076,798 | 2/1978 | Casey et al. | 424/22 |
| 4,105,034 | 8/1978 | Shalaby et al. | 128/335.5 |
| 4,122,129 | 10/1978 | Casey et al. | 260/860 |
| 4,181,983 | 1/1980 | Kulkarni | 3/1 |
| 4,272,518 | 6/1981 | Moro et al. | 424/78.06 |
| 4,631,188 | 12/1986 | Stoy | 424/422 |
| 4,780,320 | 10/1988 | Baker | 424/426 |
| 4,793,336 | 12/1988 | Wang | 128/156 |
| 4,913,903 | 4/1990 | Sudmann et al. | 424/426 |
| 4,938,763 | 7/1990 | Dunn et al. | 604/891.1 |
| 4,981,696 | 1/1991 | Loomis | 424/426 |
| 5,013,553 | 5/1991 | Southard et al. | 424/426 |
| 5,077,049 | 12/1991 | Dunn et al. | 424/426 |
| 5,154,706 | 10/1992 | Cartmell et al. | 523/111 |
| 5,266,359 | 11/1993 | Spielvogel | 523/105 |
| 5,278,201 | 1/1994 | Dunn et al. | 424/426 |
| 5,278,202 | 1/1994 | Dunn et al. | 424/426 |
| 5,324,519 | 6/1994 | Dunn et al. | 424/426 |
| 5,324,520 | 6/1994 | Dunn et al. | 424/426 |
| 5,340,849 | 8/1994 | Dunn et al. | 424/426 |
| 5,368,859 | 11/1994 | Dunn et al. | 424/426 |
| 5,409,966 | 4/1995 | Duan et al. | 523/111 |
| 5,457,141 | 10/1995 | Matsuda et al. | 528/905 |
| 5,461,124 | 10/1995 | Ritter et al. | 523/111 |
| B1 4,938,763 | 7/1995 | Dunn et al. | 424/426 |

FOREIGN PATENT DOCUMENTS

| | | |
|---|---|---|
| 0159293 (A) | 10/1985 | European Pat. Off. . |
| 0537559 (A1) | 4/1993 | European Pat. Off. . |
| 0539751 (A) | 5/1993 | European Pat. Off. . |
| 0560014 (A1) | 9/1993 | European Pat. Off. . |
| 0649662 (A1) | 4/1995 | European Pat. Off. . |
| 0281908 | 8/1990 | Germany .................. 523/111 |
| 0305175 | 3/1989 | United Kingdom ...... 523/111 |
| WO 9003768 (A1) | 4/1990 | WIPO . |
| WO 9101126 (A1) | 2/1991 | WIPO . |
| WO 9200718 (A1) | 1/1992 | WIPO . |

OTHER PUBLICATIONS

Nelson, "Prevention of Postoperative Infections", in *Total Joint Replacement*, Section III, Chapter 8, pp. 77–87, W. B. Saunders Company, 1991.
Encyclopedia of Polymer Science and Engineering, vol. 2, pp. 236–237 (Biodegradable Polymers), John Wiley & Sons, Inc. (1985).
Billmeyer, Textbook of Polymer Science (Third Edition), pp. 390–391, John Wiley & Son, New York (1984).
Gilding, Biodegradable Polymers (Chapter 9), pp. 210–232, Biocompatibility of Clinical Implant Materials (1981).
Hawley's Condensed Chemical Dictionary (11th Ed.) pp. 224, 555 and 567, Van Nostrand Reinhold Co., NY, NY (1987).
Holland, Polymers for Biodegradable Medical Devices, 1. The Potential of Polyesters and Controlled Macromolecular Release Systems, J. of Controlled Release 4: 155–180 (1986).

*Primary Examiner*—Andrew E. C. Merriam
*Attorney, Agent, or Firm*—Merchant, Gould, Smith, Edell, Welter & Schmidt

[57] ABSTRACT

A medical device which is a surgically implantable device coated with an adjunctive polymer system. The adjunctive polymer system forms a solid matrix when introduced into a human or animal body. The adjunctive polymer system can contain a drug or a medicament which is released over time from the solid matrix. The adjunctive polymer system contacts body tissue into which the surgically implantable device is implanted.

8 Claims, No Drawings

ADJUNCTIVE POLYMER SYSTEM FOR USE WITH MEDICAL DEVICE

This is a Continuation of application Ser. No. 08/457,097, filed Jun. 7, 1995 now abandoned, which is a divisional of application Ser. No. 08/226,006, now abandoned filed Apr. 8, 1994, which application is incorporated herein by reference.

BACKGROUND OF THE INVENTION

Medical devices have been developed for a large number of applications in humans and animals. These include wound closure devices such as sutures, staples and clips; wound covering devices such as bandages, fabrics, meshes, cloth or netting; wound repair devices like bone plates, orthopedic rods and screws, or catheters; and prosthetic devices such as hip, knee, and dental implants. All of these devices provide a specific function in treatment of the body. However, the devices when used alone may cause certain problems.

For example, sutures and catheters in human or animal skin are usually bandaged to prevent infection by pathogenic organisms and to absorb escaping bodily fluids. The presence of infection causing organisms on implants, such as sutures and catheters, is a particularly serious concern since bacteria are likely to become more active on foreign bodies. However, conventional bandages fail to adequately seal wounds or holes in the body where bodily fluids can escape and organisms can penetrate. Therefore, it is desireable to sufficiently seal such wounds thereby reducing the chances of infection and loss of bodily fluid. When wounds in internal tissue are sealed, it is particularly important that the seal is capable of biodegrading or bioeroding so it will not have to be surgically removed.

Wound covering devices are normally draped over the treatment site and held in place by sutures or adhesives. However, the suturing of these coverings in place is often tedious and time-consuming and not desireable in many body sites. The adhesives are normally used external to the body and not applied directly to the affected tissue but to adjacent healthy tissue because they must be removed. It is desireable that a biocompatible material could be used to adhere wound coverings such as fabrics, meshes and bandages directly to the affected tissue and be biodegradable so that it would not have to be removed as the tissue heals.

Certain implants such as screws or plates can have rough surfaces which cause abrasions on nearby tissue. Other implants such as clips and sutures can cause discomfort and may interfere with the function of nearby tissue. Accordingly, it is desirable to place a smooth coating on the rough surfaces of implants in order to decrease discomfort and reduce damage to nearby tissue.

Implanting a medical device such as an artificial hip or joint usually requires a treatment regime of antibiotics administered topically, orally and/or intravenously in order to reduce infection. Current recommendations suggest intravenously administering antibiotics for a period of 72 hours or less after implant surgery. See Total Joint Replacement, 1991, W. B. Saunders Company, Nelson, "Prevention of Postoperative Infections," pages 77–86. In addition, topical antibiotic irrigations are common during the operative procedure. Even during relatively routine procedures, such as closing a wound with sutures or staples, a topical antibacterial ointment cream such as a mixture of vancomycin, polymyxin B, and neosporin is often applied to reduce infection. Since bacteria are likely to become more active on foreign bodies, it is desirable to provide an effective antibiotic regime at the implant site rather than rely on periodic injections or administration of antibiotic. Accordingly, it is desirable to provide an implant which releases a prescribed amount of antibiotic over a predetermined period of time.

Implants may cause pain and/or tend to be rejected by the body host. Accordingly, drugs and medicaments which prevent infection, relieve pain, promote healing and suppress rejection are typically administered to patients undergoing or having undergone implant surgery. Rather than subject a patient to a regime of intravenously or orally administered drugs, it is desirable to provide at the implant site a drug or medicament which is released over a predetermined period of time to relieve pain, promote healing, suppress rejection and the like.

SUMMARY OF THE INVENTION

The present invention provides an adjunctive polymer system for coating a medical device which is a surgically implantable; a method for enhancing the compatibility of a surgically implantable device; a bandage coated with an adjunctive polymer system; a method for sealing a wound in body tissue; a medical device which is a surgically implanted device coated with a solid matrix; and a method for treating bone disorders.

The medical device is a combination of a first component which is a surgically implantable device (SID) and a second component which is an adjunctive polymer system (APS). The combination may be used in any form that will allow contact between the adjunctive polymer system and the body tissue into which the medical device is implanted. Generally, those forms include a coating or impregnation of the adjunctive polymer system upon the surgically implantable device prior to implantation; application of the adjunctive polymer system to the body tissue followed by implantation thereon of the surgically implantable device; and implantation of the surgically implantable device followed by coating thereon the adjunctive polymer system.

The first component of the medical device, namely the surgically implantable device, includes a mechanical implant used in a human or animal body. Generally, mechanical implants are used in combination with body tissue or organs temporarily, permanently, or semi-permanently, to remedy a problem and can be removed surgically or by biodegrading and/or bioeroding within the body. Exemplary implants include bandages, sutures, staples, clamps, fabric, meshes, webbing, cloth, netting, carbon fibers, artificial bones, screws, bone plates, orthopedic rods, nails, silicone valves, hip implants, knee implants, artificial hearts, replacement teeth, dental implants, catheters, and the like. Many of the above listed devices include devices, such as bandages, sutures, staples and the like, which can be applied topically and internally. For example, a bandage can be placed on exterior tissue, such as skin or mucous membrane, or on internal tissue, such as a liver. If desired, the surgically implantable device can contain a biologically active material which can be released therefrom. Suture fiber, cloth and the like can be capable of releasing drugs over time.

The second component of the medical device, namely the adjunctive polymer system, produces a solid matrix when it is contacted with water or a water-based environment which is normally found inside a human or animal body. Body tissue normally contains sufficient water or fluid to form the solid matrix. The adjunctive polymer system contains (a) a pharmaceutically acceptable, biodegradable thermoplastic polymer that is substantially insoluble in water or human or animal body fluids, and a biocompatible organic solvent which solubilizes the polymer and is miscible or dispersible in water or human or animal body fluids; or (b) a pharmaceutically acceptable, biodegradable in situ reactive prepolymer. For the thermoplastic polymer, upon contact with water or human or animal body fluids, the organic solvent disperses and the thermoplastic polymer coagulates to form a solid matrix. The in-site reactive prepolymer is mixed with a catalyst or initiator just prior to its introduction in the body where it polymerizes to form a solid implant.

The thermoplastic polymer component of the adjunctive polymer system can be any thermoplastic polymer or copolymer that is biocompatible, pharmaceutically acceptable and biodegradable by cellular action and/or by the action of body fluids. Preferably, the thermoplastic polymer is a polylactide, polyglycolide, polycaprolactone, or copolymer thereof. The organic solvent component of the adjunctive polymer system can be any solvent which solubilizes the thermoplastic polymer component and is biocompatible, pharmaceutically acceptable and soluble in water. Preferably, the organic solvent is N-methyl-2-pyrrolidone, 2-pyrrolidone, dimethyl sulfoxide, propylene carbonate and ethyl lactate due, at least in part, to their solvating ability and their biocompatibility.

The in situ reactive prepolymer component of the adjunctive polymer system can be any prepolymer that is capable of cross-linking in situ to form a thermoset polymeric or copolymeric solid which is biocompatible, pharmaceutically acceptable and biodegradable by cellular action and/or by the action of body fluids. Preferably, the in situ reactive prepolymer is an acrylic ester-terminated biodegradable prepolymer. The in situ reactive prepolymer may include a biocompatible curing agent or catalyst, which is capable of enhancing the cross-linking reaction of prepolymers. A preferred curing agent for the arcylic ester-terminated biodegradable prepolymer is benzoyl peroxide. The composition can be a neat liquid or it can include a pharmaceutically acceptable organic solvent that is soluble in water and body fluids.

The adjunctive polymer system can contain additional components such as a biologically active material which can be released from the solid matrix at a desired rate and over a desired period of time, and an agent which controls the rate of release of the biologically active material. The biologically active material includes any biologically, physiologically, or pharmacologically active substance that acts locally or systemically in a human or animal body. Exemplary biologically active materials include antibiotics, analgesics, growth promoting agents, clotting agents, anesthetics, antiseptics, antioxidants and the like. Preferably, the solid matrix releases an effective amount of biologically active agent at the implanted site to reduce infection, pain, etc. or to enhance healing, growth, etc. in local tissue. Rate modifying agents can be used to control the rate of release of the biologically active material.

The adjunctive polymer system can include a pore forming agent for forming pores in the solid matrix. Pore forming agents include organic solvents and water soluble materials which dissolve in human or animal body fluid. It may be desirable to create pores in the solid matrix to allow the solid matrix to be capable of passing fluid or allowing tissue ingrowth, or to control the rate of release of biologically active material from the solid matrix.

The combination of the implantable device and the adjunctive polymer system can be used as the implantable device is normally intended. The adjunctive polymer system enhances the compatibility of the surgically implantable device with body tissue. For example, the adjunctive polymer system is capable of providing a smooth surface on implants thereby reducing the occurrence of abrasions on nearby tissue caused by rough edges on implants. It can be applied to metallic screws, nails, bone plates, orthopedic rods, dental implants, sutures, staples, clips, bandages and the like to cover rough surfaces and/or to hold them in place. When applied over suture or staple knots, the adjunctive polymer system additionally helps prevent the knots from slipping.

In addition, the adjunctive polymer system can penetrate into holes/voids in tissue created by an implant and act as caulking to provide a tight seal around the implant which reduces loss of body fluids and chances of infection. For example, the adjunctive polymer system can be applied around transcutaneous and percutaneous catheter sites where it seeps into the surgical incision, solidifies, adheres the catheter to the tissue and forms a tight seal to reduce chances of bacteria infection. Similarly, the adjunctive polymer system can be applied around metallic screws, bone plates, orthopedic rods, dental implants and the like to fill voids, provide better adhesion or adaptation and/or retention, and to reduce chances of infection. It can also be used for colostomy where there is an opening to the stomach or intestine that needs protection.

The adjunctive polymer system can be applied as a light or thin coating as well as a thick coating. The adjunctive polymer system can be applied to an implantable medical device before or after it is implanted, and can be applied by brushing, spraying, dipping, extruding, injecting and the like, and by means including a syringe, needle, cannula, pump, and the like.

Wound dressings and repair devices including surgical fabric, mesh and the like can be used in combination with the adjunctive polymer system and applied to organs or tissue as a patch or covering. Such fibrous devices can be used, for example, for vascular grafts and for healing wounds. The fabric or mesh provides strength and the adjunctive polymer system provides adhesion.

The fibrous device can be soaked in the adjunctive polymer system before it is applied to the tissue or organ. Alternatively, the adjunctive polymer system can be applied directly to the wound and, if desired, allowed to partially coagulate, and the fibrous device can be applied thereon, or the fibrous device can be applied directly to the wound and the adjunctive polymer system can be applied over the fibrous device. If desired, the adjunctive polymer system can penetrate into the wound and help hold the tissue together while providing a seal which resists contamination during the healing process.

Upon contact with water or human or animal body fluid, the adjunctive polymer system coagulates or cures into a solid matrix but remains in contact with the implantable device and the organ or tissue. The length of time between application of the adjunctive polymer system to body tissue and formation of the solid matrix is, for the thermoplastic polymer system, a function of moisture level in or near the tissue, and the diffusion or dispersion rate of the solvent from the polymer. The rate can be accelerated by adding external water. For the thermoset polymer system, the cure time is a function of the reaction rate of the reactive prepolymer, etc. Over time, the solid matrix biodegrades or bioerodes within the body and is metabolized and discharged without the need for further surgery. Many implantable devices, such as sutures and bandages, can similarly be designed to biodegrade or bioerode within a body.

Bone disorders can be treated by placing the adjunctive polymer system containing a biologically active material directly into bone marrow via an osteostent or osteoport. For example, chronic anemia can be treated by injecting the adjunctive polymer system containing erythropoietin (EPO) into an osteostent or osteoport where it contacts bone marrow. As the adjunctive polymer system forms a solid matrix, the erythropoietin begins diffusing therefrom stimulating the marrow stem cells to produce more red blood cells.

DETAILED DESCRIPTION OF THE INVENTION

As used herein, the phrase "human or animal" refers to any creature including a mammal, an animal, a bird, a reptile, etc.

The medical device according to the present invention is a combination of a first component which is a surgically implantable device and a second component which is an adjunctive polymer system. The combination can be used practically anywhere within the body of a patient. Exemplary places for use include soft tissue such as muscle or fat; hard tissue such as bone; or a cavity or pocket such as the periodontal, oral, vaginal, rectal, nasal, or the cul-de-sac of the eye. Additional places in the body where the combination can be used will be readily appreciated in view of the following teaching of the present invention. The Surgically Implantable Device The first component, namely the surgically implantable device, includes structural or prosthetic devices such as knee and hip implants, metal plates, screws, nails, stainless steel rods, bone replacement material, silicone valves or other silicone prothesis, artificial hearts, replacement teeth and jaw replacement and the like; devices which hold tissue in place such as sutures, staples, cloth, netting, webbing and the like; and devices designed to permit injection and/or withdrawal of fluids or to keep a passage open such as catheters and the like.

The surgically implantable device can incorporate a biologically active material which can be released over time in a body. The type and amount of biologically active material which can be incorporated into the surgically implantable device can be determined according to the teachings of this invention with respect to the adjunctive polymer system or according to known products. For example, suture fiber can contain a biologically active material which can be released into tissue over time.

The various surgically implantable devices which can be used in combination with the adjunctive polymer system will be readily appreciated in view of the following teaching of the present invention.
The Adjunctive Polymer System The second component, namely the adjunctive polymer system, contains (a) a pharmaceutically acceptable, biodegradable thermoplastic polymer that is substantially insoluble in water or human or animal body fluids, and a biocompatible organic solvent which solubilizes the polymer and is miscible or dispersible in water or human or animal body fluids; or (b) a pharmaceutically acceptable, biodegradable in situ reactive prepolymer; or both in admixture. For the thermoplastic polymer, upon contact with water or human or animal bodily fluids, the organic solvent disperses and the polymer coagulates to form a solid matrix. The in situ reactive prepolymer when combined with a curing agent just prior to insertion into the body polymerizes or crosslinks to form a solid matrix. The solid matrix is alternatively referred to herein as "the matrix" and "the polymer matrix."

The adjunctive polymer system forms the solid matrix in the presence of water or human or animal body fluids as the organic solvent disperses from the adjunctive polymer system and the thermoplastic polymer coagulates, or as the in situ reactive prepolymer cures to form a thermoset polymer. If desired, a biologically active material can be present in the adjunctive polymer system and, subsequently, incorporated into the solid matrix where it is released over time. In addition, the adjunctive polymer system can contain an agent that helps control the rate of release of the biologically active material and/or an agent which affects the pore sizes in the solid matrix. Thus, if a biologically active material is present in the solid matrix having pores, it diffuses through the fluid-filled pores at a controlled rate. The rate at which the biologically active material departs the solid matrix can be a function of the rate at which the polymer biodegrades if the biologically active material cannot diffuse through the polymer matrix and if no pores are present or if the pores are too small.

The adjunctive polymer system and the solid matrix formed therefrom are pharmaceutically acceptable and biodegradable and/or bioerodable within the body of a human or animal. The biodegradation enables a patient to metabolize the polymer matrix so that it can be discharged by the patient without the need for further surgery to remove it. Because the adjunctive polymer system and solid matrix are biocompatible, the insertion process and the presence of the adjunctive polymer system and, subsequently the solid matrix, within the body do not cause substantial tissue irritation or necrosis at the implant site.

The present invention is particularly advantageous because of the adhesive properties of the biodegradable, biocompatible adjunctive polymer system which allows it to be used as an adhesive in combination with human or animal tissue. As the adjunctive polymer system forms the solid matrix in the presence of water or human or animal body fluid, it remains adhered to tissue it contacted in the liquid state but does not adhere to other tissue it may contact after solidifying. The coating on the solid matrix can be smooth. This is important when using an implantable device and adjunctive polymer system in a tight place where other surgical adhesives would cause problems by adhering to nearby organs or tissue.

The adjunctive polymer system can have a wide range of viscosities depending on the particular use for which it is designed. For example, the viscosity of the adjunctive polymer system can be as low as water or as high or higher than molasses. The viscosity can be altered by selection of the polymer or in situ reactive prepolymer or other component used therein and by the concentration of the polymer in the biocompatible solvent. It may be readily appreciated how polymer molecular weight and degree of crosslinking affect viscosity. Thus, the viscosity of the adjunctive polymer system can be designed for a particular application. The adjunctive polymer system can have a low viscosity when it is intended to form a thin film on an implanted medical device. This may be necessary when it is being used in a compact place such as a joint or when it is intended to seep into small holes in tissue created by sutures, staples, catheters and the like. Alternatively, the adjunctive polymer system can be more viscous when it is intended to be applied as a thicker coat to seal a wound or provide a barrier against the rough edges of a bone screw.

The following is a more detailed identification of ingredients which can make up the adjunctive polymer system useful in the present invention.

a) Pharmaceutically Acceptable, Biodegradable Thermoplastic Polymer

The pharmaceutically acceptable, biodegradable thermoplastic polymer which can be used in the adjunctive polymer system is insoluble in water or human or animal body fluids. Preferably, the thermoplastic polymer is substantially insoluble, more preferably essentially completely insoluble in water and body fluids. Thus, in an aqueous media, the polymer coagulates and forms a solid matrix.

The thermoplastic polymer can be a homopolymer, copolymer, terpolymer, etc. Examples of suitable thermoplastic polymers which can be used to form the solid matrix include polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid) polymers, polymaleic anhydrides, poly(methylvinyl) ethers, poly(amino acids), chitin, chitosan, and copolymers, terpolymers, or combinations or mixtures of the above materials, and with other materials.

Preferred thermoplastic materials are the polylactides, polyglycolides, polycaprolactones, and copolymers and terpolymers thereof. These polymers can be used to advantage in the adjunctive polymer system in part because they show excellent biocompatibility. They produce little, if any, tissue irritation, inflammation, necrosis, or toxicity. In the presence of water, these polymers produce lactic, glycolic, and hydroxycaproic acid, respectively, which are readily metabolized by the body. The polylactides and polycaprolactones can also incorporate glycolide monomer to enhance the resulting polymer's degradation.

Depending on the desired softness and flexibility of the resulting solid matrix, rate and extent of bioactive material release, rate of degradation, and the like, the amount and type of polymer can be varied to produce the desired result. For example, for a relatively soft and flexible polymer system, copolymers with a low Tg can be used, primarily the lactide/caprolactone copolymers. The ratio of glycolide to lactide to caprolactone can also be varied to effect water adsorption, which increases with an increasing amount of the more hydrophilic monomer. The hydrophilic character of these monomers increases in the series as caprolactone <lactide <glycolide.

The solubility or miscibility of a thermoplastic polymer in the organic solvent of the adjunctive polymer system will vary according to factors such as crystallinity, hydrophilicity, capacity for hydrogen bonding and molecular weight of the polymer. Consequently, the molecular weight and the concentration of the polymer in the solvent are adjusted to achieve desired miscibility, as well as a desired release rate for the incorporated bioactive material. Highly preferred thermoplastic polymers are those having solubility parameters such as a low degree of crystallization, a low degree of hydrogen bonding, low solubility in water, and high solubility in organic solvents.

According to the practice of the invention, the adjunctive polymer system of pharmaceutically acceptable, biodegradable thermoplastic polymer and solvent is a stable liquid substance. If a bioactive material is used, either a homogenous solution of the bioactive material in organic solvent, or a suspension or dispersion of the bioactive material in the solvent results. In either case, the polymer is substantially soluble in the organic solvent. Upon placement into an aqueous medium, the solvent will dissipate and the polymer will solidify to form the solid polymeric matrix containing, if desired, a bioactive material.

b) Biocompatible Organic Solvents

The biocompatible organic solvent which can be used in the adjunctive polymer system is capable of solubilizing the thermoplastic polymer and is miscible or dispersible in water or human or animal body fluids. Preferably, the solvent causes relatively little, if any, tissue irritation or necrosis at the site of the injection and implantation. The solvent is water-soluble so that it will quickly disperse from the polymeric composition into an aqueous medium such as body fluids. Concomitant with the dispersion of solvent the polymer coagulates into the solid matrix. As the polymer coagulates the solvent dispersion causes pore formation within the polymer composition. Generally, the coagulated polymer will be microporous.

The degree of polarity of the solvent should be effective to provide at least about 10% solubility in water, and to dissolve, disperse or suspend the polymer component. The concentration of polymer in solution can be adjusted such that the solvent will rapidly and effectively dissipate. This concentration can range from about 0.01g/ml to that of a saturated solution Suitable solvents include those liquid organic compounds meeting the foregoing criteria. Examples include, but are not limited to, N-methyl-2-pyrrolidone (NMP); 2-pyrrolidone (2-pyrol); $C_2$–$C_6$ alkanols; 2-ethoxyethanol; alkyl esters such as 2-ethoxyethyl acetate, ethyl acetate, ethyl lactate, ethyl butyrate, diethyl malonate, diethyl glutarate, tributyl titrate, acetyl-tri-n-hexylcitrate, diethyl succinate, tributyrin, isopropyl myristate; carbonates such as propylene carbonate, dimethyl carbonate; ethylene glycol dimethyl ether; propylene glycol; 1,3-butylene glycol; ε-caprolactone; γ-butyrolactone; dimethylformamide; dimethylacetamide; dimethyl sulfoxide; dimethyl sulfone; cyclic alkyl amides such as caprolactam; decylmethylsulfoxide; oleic acid; N,N-dimethyl-m-toluamide; 2,2 dimethyl-1,3-dioxolane-4-methanol; and 1-dodecylazacycloheptan-2-one. The preferred solvents are N-methyl-2-pyrrolidone, 2-pyrrolidone, dimethyl sulfoxide, propylene carbonate and ethyl lactate due, at least in part, to their solvating ability and their biocompatibility.

The solvents for the adjunctive polymer system are chosen for compatibility and appropriate solubility of the polymer. Lower molecular weight thermoplastic polymers will normally dissolve more readily in the solvents than high molecular weight polymers. As a result, the concentration of a thermoplastic polymer dissolved in the various solvents differs depending upon type of polymer and its molecular weight. Conversely, the higher molecular weight thermoplastic polymers will tend to coagulate or solidify faster than the very low molecular weight thermoplastic polymers. Moreover, the higher molecular weight polymers tend to give higher solution viscosities than the low molecular weight materials. Thus, depending on the desired application of the adjunctive polymer system, the molecular weight and the concentration of the polymer in the solvent are controlled.

A solvent mixture can be used to increase the coagulation rate of thermoplastic polymers that exhibit a slow coagulation rate. In such a system one component of the mixture is typically a good solvent for the thermoplastic polymer, and the other component is a poorer solvent or a nonsolvent. The two liquids are mixed at a ratio such that the thermoplastic polymer is still soluble, but precipitates with the slightest increase in the amount of nonsolvent, such as water in a physiological environment. By necessity, the solvent system must be miscible with both the thermoplastic polymer and water. An example of such a binary solvent system is the use of NMP and ethanol for low molecular weight DL-PLA. The addition of ethanol to the NMP/polymer solution increases its coagulation rate significantly.

When the thermoplastic liquid composition is added to the aqueous medium, the organic solvent diffuses into the surrounding medium (body fluids or an external water medium) and the polymer coagulates to form the solid matrix having pores, preferably micropores. The more or less simultaneous diffusion and coagulation produce a matrix with a core and skin structure that in part is believed to be a factor in the establishment of the desired control of rate and extent of release of biologically active material, if present.

c) Pharmaceutically Acceptable, Biodegradable In Situ Reactive Prepolymer

The pharmaceutically acceptable, biodegradable in situ reactive prepolymer which can be used in the adjunctive polymer system can cure in the presence of water or body fluids to form a thermoset polymer. If desired, a curing agent such as a curing catalyst can be used to cure the reactive prepolymer. The resulting thermoset polymer is pharmaceutically acceptable, biodegradable and insoluble in water or human or animal body fluids.

The reactive prepolymers can be liquid and/or combined with a biocompatible organic solvent as described above to provide a liquid. Any of the biodegradable polymers previously described for the thermoplastic system and having or being adapted to have cross-linkable or curable functional groups can be used. Prepolymers can be used. However, low molecular weight oligomers are preferred. These are usually liquids at room temperature. They are also preferably functionalized with end groups that are reactive with acryloyl chloride to produce acrylic ester capped prepolymers. Acrylic prepolymers for use in the liquid composition may be synthesized according to a variety of methods including, but not limited to, reaction of a carboxylic acid, such as acrylic or methacrylic acid, with an alcohol; reaction of a carboxylic acid ester, such as methyl acrylate or methyl methacrylate, with an alcohol by transesterification; reaction of a carboxylic acid chloride such as acryloyl chloride with an alcohol, and reaction of an isocyanatoalkyl acrylate, such as isocyanatoethyl methacrylate, with an alcohol. These methods are known in the art.

A preferred biodegradable polymer system is produced from poly(DL-lactide-caprolactone), or "DL-PLC." Low molecular weight polymers or oligomers produced from these materials are flowable liquids at room temperature. To prepare the DL-PLC polymer matrix, hydroxy-terminated PLC prepolymers are initially synthesized via copolymerization of DL-lactide or L-lactide and ε-caprolactone with a multifunctional polyoyl initiator and a catalyst. Catalysts useful for the preparation of these prepolymers are preferably basic or neutral ester-interchange (transesterification catalysts). These include, for example, metallic esters of carboxylic acids containing up to 18 carbon atoms, such as formic, acetic, lauric, stearic, and benzoic acids. Stannous octoate and stannous chloride are preferred catalysts.

In the above reaction, if a bifunctional polyester is desired, a bifunctional polyol chain initiator such as ethylene glycol is employed. If a trifunctional polyester is desired, a trifunctional polyol chain initiator such as trimethylolpropane is employed. The amount of chain initiator used determines the resultant molecular weight of the polymer or copolymer. For example, a high concentration of a bifunctional chain initiator provides an initiator molecule for each polymer chain, whereas a low concentration of bifunctional initiator provides one initiator molecule for every two polymer chains.

The diol or polyol-terminated prepolymers are converted to acrylic-ester prepolymers by any suitable method, as for example, by acylation of the alcohol terminal end with acryloyl chloride by means of a Schotten-Baumann technique.

A curing agent, such as a catalyst, may be added to the acrylic prepolymer mixture to enhance cross-linking of the prepolymers and the subsequent solidification of the resulting polymer to form a matrix. For example, a peroxide such as benzoyl peroxide may be added to the acrylic prepolymer mentioned above. Optionally, other acrylic monomers may be added to the acrylic prepolymer mixture before adding the curing agent.

This thermoset polymer forming system can be used wherever a bioactive material can be advantageously released from a biodegradable implant. Because the reactive prepolymer remains a liquid for a short time after addition of the curing agent, the liquid prepolymer/bioactive material/curing agent mixture preferably is immediately thereafter inserted into the aqueous medium. The curing steps can be accomplished using known means, e.g., by exposure to radiation, with or without a curing agent.

The thermoset liquid composition can contain one or more materials to form a microporous matrix. These include water-soluble materials such as sugars, salts, and polymers, or solvents. If a solvent is used, the solvent may be present in an amount suitable to form a porous matrix, but not so high as to substantially dilute the prepolymers such that the resultant polymer would be only lightly cross-linked.

d) Biologically Active Materials

The terms "drug," "medicament," or "bioactive material" (i.e., biologically active material) as used herein include, biologically, physiologically, or pharmacologically active substances that act locally or systemically in the human or animal body.

When a biologically active agent is to be released by the solid matrix, the agent is dissolved in the adjunctive polymer system to from a homogenous solution or dispersed in the adjunctive polymer system to form a suspension. Various forms of the medicaments or biologically active materials can be used which are capable of being released from the solid matrix into adjacent tissues or fluids. The medicaments are at least very slightly water soluble, preferably moderately water soluble, and are diffusible through the polymeric composition. They can be acidic, basic, or amphoteric salts. They can be nonionic molecules, polar molecules, or molecular complexes capable of hydrogen bonding. They can be in the form of ethers, esters, amides and the like, or polymer drug conjugates and the like, which are biologically activated when introduced into the human or animal body.

Generally, any drugs or bioactive materials that can be dissolved or dispersed in an aqueous environment can be utilized in the adjunctive polymer system. Representative drugs or bioactive materials that can be used in the adjunctive polymer system or solid matrix of the present invention include, but are not limited to, peptide drugs, protein drugs, desensitizing materials, antigens, anti-infective agents such as antibiotics, antimicrobial agents, antiviral, antibacterial, antiparasitic, antifungal substances and combination thereof, antiallergenics, androgenic steroids, decongestants, hypnotics, steroidal anti-inflammatory agents, anticholinergics, sympathomimetics, sedatives, miotics, psychic energizers, tranquilizers, vaccines, estrogens, progestational agents, humoral agents, prostaglandins, analgesics, antispasmodics, antimalarials, antihistamines, cardioactive agents, nonsteroidal anti-inflammatory agents, antiparkinsonian agents, antihypertensive agents, β-adrenergic blocking agents, nutritional agents, and the benzophenanthridine alkaloids. The agent may further be a substance capable of acting as a stimulant, sedative, hypnotic, analgesic, anticonvulsant, and the like.

The adjunctive polymer system can contain a large number of biologically active agents either singly or in combination. The biologically active agents can be in a controlled release component which is dissolved, dispersed or entrained in the adjunctive polymer system. The controlled release component can include microstructures, macrostructures, conjugates, complexes, low water-solubility salts and the like. Microstructures include nanoparticles, cyclodextrins, microcapsules, micelles, liposomes and the like. Macrostructures include fibers, beads and the like. Controlled release compositions are disclosed in copending U.S. patent application Ser. No. 08/225,140, filed Apr. 8, 1994, entitled "Liquid Delivery Compositions," the disclosure of which is incorporated herein by reference.

It is preferred that the biologically-active agents contained and released from the adjunctive polymer system are those that supplement and/or improve the benefits of the medical device with which the adjunctive polymer system is combined. Examples of these biologically-active agents include, but are not limited to:

Anti-inflammatory agents such as hydrocortisone, prednisone, fludrotisone, triamcinolone, dexamethasone, betamethasone, and the like.

Anti-bacterial agents such as penicillins, cephalosporins, vancomycin, bacitracin, polymycins, tetracyclines, chloramphenicol, erythromycin, streptomycin, quinolone, and the like.

Antifungal agents such as nystatin, gentamicin, miconazole, tolnaftate, undecyclic acid and its salts, and the like.

Analgesic agents such as salicylic acid, salicylate esters and salts, acetaminophen, ibuprofen, morphine, phenylbutazone, indomethacin, sulindac, tolmetin, zomepirac, and the like.

Local anesthetics such as cocaine, benzocaine, novocaine, lidocaine, and the like.

The bioactive material may also be a substance, or metabolic precursor thereof, which is capable of promoting growth and survival of cells and tissues, or augmenting the activity of functioning cells, as for example, blood cells, neurons, muscle, bone marrow, bone cells and tissues, and the like. For example, the bioactive material may be a nerve growth promoting substance, as for example, a ganglioside, phosphatidylserine, a nerve growth factor, brain-derived neurotrophic factor. The bioactive material may also be a growth factor for soft or fibrous connective tissue as, for example, a fibroblast growth factor, an epidermal growth factor, an endothelial cell growth factor, a platelet derived growth factor, an insulin-like growth factor, a periodontal ligament cell growth factor, cementum attachment extracts, and fibronectrin.

To promote bone growth, the biologically active material may be an osteoinductive or osteoconductive substance. Suitable bone growth promoting agents include, for example, osteoinductive factor (OIF), bone morphogenetic protein (BMP) or protein derived therefrom, demineralized bone matrix, and releasing factors thereof. Further, the agent may be a bone growth promoting substance such as hydroxyapatite, tricalcium phosphate, a di- or polyphosphonic acid, an anti-estrogen, a sodium fluoride preparation, a substance having a phosphate to calcium ratio similar to natural bone, and the like. A bone growth promoting substance may be in the form, as for example, of bone chips, bone crystals or mineral fractions of bone and/or teeth, a synthetic hydroxyapatite, or other suitable form. The agent may further be capable of treating metabolic bone disorders such as abnormal calcium and phosphate metabolism by, for example, inhibiting bone resorption, promoting bone mineralization, or inhibiting calcification. The active agent may also be used to promote the growth and survival of blood cells, as for example, a colony stimulating factor, and erythropoietin.

The biologically-active agent may be included in the compositions in the form of, for example, an uncharged molecule, a molecular complex, a salt, an ether, an ester, an amide, polymer drug conjugate, or other form to provide the effective biological or physiological activity.

The bioactive material can be miscible in the polymer and/or solvent to provide a homogenous mixture with the polymer, or insoluble in the polymer and/or solvent to form a suspension or dispersion with the polymer. It is highly preferred that the biologically active material be combined with the thermoset polymer forming composition almost immediately prior to administration of the composition to the implant site. It is further preferred that the bioactive material does not contain functional groups that could interfere with the cross-linking reaction of the thermosetting polymer. These conditions are readily determined by those of skill in the art simply by comparing the structure of the bioactive material and the reacting moieties of the thermosetting polymer.

Upon formation of the solid matrix from the adjunctive polymer system, the biologically active material becomes incorporated into the polymer matrix. The bioactive material will be released from the matrix into the adjacent tissues or fluids by diffusion and polymer degradation mechanisms. Manipulation of these mechanisms also can influence the release of the bioactive material into the surroundings at a controlled rate. For example, the polymer matrix can be formulated to degrade after an effective and/or substantial amount of the bioactive material is released from the matrix. Release of a material having a low solubility in water, as for example a peptide or protein, typically requires the degradation of a substantial part of the polymer matrix to expose the material directly to the surrounding tissue fluids. Thus, the release of the biologically active material from the matrix can be varied by, for example, the solubility of the bioactive material in water, the distribution of the bioactive material within the matrix, or the size, shape, porosity, solubility and biodegradability of the polymer matrix, among other factors. The release of the biologically active material can facilitate pore formation. The release of the biologically active material from the matrix is controlled relative to its intrinsic rate by varying the polymer composition, molecular weight, and/or polymer concentration, and by adding a rate modifying agent to provide a desired duration and rate of release, as described above.

The polymer system is formulated to contain the bioactive material in an amount effective to provide a desired biological, physiological and/or therapeutic effect. The "effective amount" of a biologically active material incorporated into the polymeric composition of the invention depends on a variety of factors, such as the desired release profile, the concentration of bioactive material required for a desired biological effect, and the period of time over which the bioactive material needs to be released for desired treatment. Ultimately, this amount is determined by the patient's physician who will apply his experience and wisdom in prescribing the appropriate kind and amount of bioactive material to provide therapy for the patient. There is generally no critical upper limit on the amount of bioactive material incorporated into the polymer solution. The only limitation is a physical limitation for advantageous application, i.e., the bioactive material should not be present in such a high concentration that the solution or dispersion viscosity is too high for use. The lower limit of bioactive material incorporated into the polymer system typically depends only on the activity of the bioactive material and the period of time desired for treatment.

e) Pore Forming Agent

Other additives can be used to advantage in further controlling the pore size in the solid matrix, which influences the structure of the matrix and the release rate of a bioactive material or the diffusion rate of body fluids. For example, if the thermoplastic polymer liquid composition is too impervious to water or tissue ingrowth, a pore-forming agent can be added to generate additional pores in the matrix. Any biocompatible water-soluble material can be used as the pore-forming agent. These agents can be either soluble in the adjunctive polymer system or simply dispersed within it. They are capable of dissolving, diffusing or dispersing out of both the coagulating and/or reacting polymer matrix whereupon pores and microporous channels are generated. The amount of pore-forming agent (and size of dispersed particles of such pore-forming agent, if appropriate) within the adjunctive polymer system will directly affect the size and number of the pores in the polymer matrix.

Pore-forming agents include any pharmaceutically acceptable organic or inorganic substance that is substantially miscible in water and body fluids and will dissipate from the forming and formed matrix into aqueous medium or body fluids or water-immiscible substances that rapidly degrade to water soluble substances. The pore-forming agent may be soluble or insoluble in the thermoset polymer liquid composition of the invention. It is further preferred that the pore-forming agent is miscible or dispersible in the organic solvent to form a uniform mixture. Suitable pore-forming agents include, for example, sugars such as sucrose and dextrose, salts such as sodium chloride and sodium carbonate, and polymers such as hydroxylpropylcellulose, carboxymethylcellulose, polyethylene glycol, and polyvinylpyrrolidone. The size and extent of the pores can be varied over a wide range by changing the molecular weight and percentage of pore-forming agent incorporated into the polymer system.

Combination of Surgically Implantable Device and Adjunctive Polymer System

The adjunctive polymer system can be applied by any convenient technique. For example, the adjunctive polymer system can be applied by brushing, spraying, extruding, dipping, injecting and the like, and by means including a syringe, needle, cannula, pump, catheter and the like. The adjunctive polymer system can be applied in the form of a film, caulk, etc. However, to increase adhesion to body tissue, it may be desirable to remove excess water or body fluid from the surface of the tissue. Although the body tissue can and should be moist, it should not have a layer of fluid thereon if it is intended that the adjunctive polymer system adhere thereto. Alternatively, if it is undesirable for the adjunctive polymer system to adhere to body tissue when it is functioning, for example as caulk, it may be desirable to add additional water to the tissue surface.

The adjunctive polymer system can be applied to the implantable device at any time before, during, or after implantation. For example, it may be desireable to apply the adjunctive polymer to a catheter, package the coated catheter in a shrink-wrap film, and store the packaged catheter until it is used. Similarly, a bandage can be packaged in combination with the adjunctive polymer system for future use. Alternatively, it may be desirable to apply the adjunctive polymer system over an implant, such as a bone screw or a suture line, or to tissue before implant surgery.

In the presence of sufficient water or body fluid, the adjunctive polymer system coagulates into a solid matrix. If desired, the amount of water in contact with the adjunctive polymer system can be controlled so as to control the rate of solid matrix formation.

In one embodiment of the present invention, the combination of the adjunctive polymer system and the implantable device holds tissue in place. Conventional implantable devices used to hold tissue together can be used in the present invention. Such devices include sutures, ligatures, staples, clips, bandages, webbing and the like. However, by coating the adjunctive polymer system on such devices, one can, as desired, advantageously increase the adhesion and/or adaptation of the device to the tissue, seal the wound to reduce loss of body fluid and chances of infection, provide a smooth surface over the device, and administer drugs or medicaments directly at the desired site. As discussed above, biologically active agents can be added to the adjunctive polymer system to reduce infection, promote healing, relieve pain, etc.

Generally, the adjunctive polymer system can be applied to sutures, staples and the like by brushing and spraying. However, the adjunctive polymer system can be applied by dipping or drawing the suture filament through the adjunctive polymer system before it is used to hold tissue together. Advantageously, the adjunctive polymer system seeps or penetrate into the holes created by the sutures or staples, and seals the holes thereby preventing fluids such as blood, urine, bowel material and the like from leaking out through the suture holes and bacteria or other contaminant from entering the wound. Alternatively, the adjunctive polymer system can be applied to an area before or during suturing to help provide adhesion and/or to quickly administer a biologically active agent thereto.

When applied to incised or torn tissue, the adjunctive polymer system can help adhere the tissue and to seal the wound to prevent body fluid from leaking out and to prevent germs or other debris from contaminating the wound. As the adjunctive polymer system penetrates into the wound, it mixes with water or body fluids and coagulates, or cures, into a solid matrix. Generally, in internal tissues and organs such as arteries and veins, liver, pancreas, etc., there is usually sufficient body fluid within the tissue or organ to completely form the solid matrix. However, in some situations, there may not be enough body fluid present to quickly and completely form the solid matrix. For example, when the adjunctive polymer system covers exposed sutures holding the outer layer of skin together, it may be helpful to add water to the adjunctive polymer system to increase the rate of formation of the solid matrix.

Applying the biodegradable adjunctive polymer system as a film over exposed sutures to prevent penetration of bacteria from outside the body is particularly important in exterior wounds, dental surgery, throat surgery, and the like, since the sutures would otherwise be exposed to the atmosphere.

In addition, the adjunctive polymer system can be used to improve knot retention in sutures and staples, and to ensure that clips and clamps remain secure for a desired length of time. Since suture knots tend to loosen, it is desirable to apply a biodegradable composition thereto which adheres to the knot allowing it to hold more firmly.

Similarly, the adjunctive polymer system can be used with catheters such as transcutaneous and percutaneous catheters. The adjunctive polymer system can be applied around the catheter site where it seeps into the surgical incision, solidifies, adheres the catheter to the tissue and forms a tight seal to prevent bacterial infection. As discussed above, a catheter can be coated with the adjunctive polymer system and stored until it is used, or the adjunctive polymer can be applied to the wound site as caulk. Alternatively, the adjunctive polymer system can be applied to body tissue before the catheter is implanted. Thus, as the catheter is inserted the solid matrix forms around the wound site. Similarly, the adjunctive polymer system can be used for colostomy where there is an opening to the stomach or intestines that needs protection.

The adjunctive polymer system can be applied to other medical devices such as metallic screws, bone plates, orthopedic rods, dental implants and the like to enhance adaptation to body tissue. The adjunctive polymer system can help the device adhere to tissue and can be applied over rough surfaces to prevent abrasion to other tissue. The adjunctive polymer system can act as a caulking material to fill voids created between the device and body tissue and to provide a desired administration rate of biologically active agent at the desired site.

When used near or in conjunction with bone tissue, the adjunctive polymer system preferably contains a biologically active agent to prevent infection and aid in healing. For example, growth factors can advantageously be used with sintered metal or hydroxyapatite coatings that are porous in that the controlled release of the factor would provide better bone ingrowth. The same holds for other devices in which soft tissue ingrowth is needed such as muscle or ligament repair.

The adjunctive polymer system can be used for treating bone disorders. For example the adjunctive polymer system can contain erythropoietin (EPO) and can be placed in living bone marrow to treat patients suffering from chronic anemia. Generally, the adjunctive polymer system is injected into the living bone marrow through an osteostent or osteoport. The EPO stimulates erythrogenesis.

The invention will be further described with reference to the following specific examples which are not intended to limit the scope of invention.

EXAMPLE 1
(The Adjunctive Polymer System)

Adjunctive polymer systems A–G can be prepared by mixing the ingredients described below in a polyethylene container at room temperature.

System A: 50:50 Poly(DL-lactide-co-caprolactone) (20 g) N-methyl-2-pyrrolidone (80 g)

System B: 75:25 Poly (DL-lactide-co-glycolide) (40 g) N-methyl-2-pyrrolidone (60 g)

System C: Poly (DL-lactide) (40 g) N-methyl-2-pyrrolidone (60 g)

System D: 50:50 Poly (DL-lactide-co-caprolactone) (15 g) N-methyl-2-pyrrolidone (80 g) Vancomycin (5 g)

System E: 50:50 Poly (DL-lactide-co-glycolide) (40 g) N-methyl-2-pyrrolidone (50 g) Demineralized bone matrix (10 g)

System F: Acrylic terminated copolymer of 15:85 poly (DL-lactide-cocaprolactone) (9.9 g) Benzoyl peroxide (0.1 g)

System G: 50:50 Poly(DL-lactide-co-gylcolide) (50 g) N-methyl-2-pyrrolidone (50 g) Erythropoietin (10 g)

EXAMPLE 1

A dog's leg can be shaved and prepared for introduction of a transcutaneous catheter. The catheter can be inserted and System A sprayed on the wound site to form a film which will solidify into a matrix in about 20 seconds.

The solid matrix will tightly adhere to the skin tissue and the catheter.

EXAMPLE 2

A pig can be anesthetized, and a half inch incision made in the liver. The incision can be sutured and System B brushed over the suture line to form a film which will solidify into a solid matrix in about 2 minutes. The film will adhere to the liver tissue and the sutures, and seal the wound.

EXAMPLE 3

A dog can be anesthetized, and a segment of bone removed from the tibia of one leg. A stainless steel plate can be attached to the two sections of the tibia with bone screws. System C can then be brushed over the bone plate and screws to completely coat them. The liquid polymer will solidify into a solid matrix in about 2 minutes and will adhere tightly to the plates and screws to provide a smooth surface.

EXAMPLE 4

A rabbit can be anesthetized and a small section of the back shaved. A half inch incision can be made in the back and sutured together with silk sutures. System D can be sprayed over the wound and suture site using an aerosol system. The liquid polymer will penetrate into the wound and around the sutures to form a 20 µm film and solidify in about 20 seconds.

EXAMPLE 5

A dog can be anesthetized and a small drill hole made in the molar section of the mandible. System E can then be applied to the surface of the drill hole using a small syringe. The base section of the dental implant can be immediately screwed into the drill hole where the liquid polymer completely coats the interface between the implant and the bone tissue and solidify to form a tight seal and matrix for delivery of the demineralized bone matrix.

EXAMPLE 6

A dog can be anesthetized and a section of a vein removed. A vascular graft made with a Dacron polyester mesh can be soaked in System F and sutured in place where the liquid prepolymer cures in 10 minutes to form a nonpervious graft coated with a biodegradable polymer.

EXAMPLE 7

A rabbit can be anesthetized and a small drill hole made in the tibia such that it penetrates to the marrow. An osteostent can be screwed into the drill hole and the tissue sutured in place. System G can then be injected into the osteostent device through the injection port. The liquid polymer will solidify with the osteostent in about 2 minutes where the drug will slowly release into the marrow space.

What is claimed is:

1. A coated wound dressing for sealing a wound in an internal tissue or organ when placed in contact with the wound, comprising: a fibrous wound dressing coated with an adjunctive polymer system to form the coated wound dressing, wherein the adjunctive polymer system comprises a pharmaceutically acceptable, biodegradable thermoplastic polymer that is insoluble in water or body fluids mixed with a biocompatible organic solvent which solubilizes the polymer and is miscible to dispersible in water or body fluids and capable of dissipating or dispersing from the adjunctive polymer system into surrounding tissue fluid whereupon the organic solvent dissipates or disperses into the surrounding tissue and the thermoplastic polymer coagulates to form a solid matrix, the proportion of thermoplastic polymer and solvent, and the polymer molecular weight being selected so as to provide said dissipation or dispersion and said coagulation.

2. The wound dressing according to claim 1, wherein the fibrous wound dressing is selected from the group consisting of fabric, mesh, webbing, cloth, net and combinations thereof.

3. The wound dressing according to claim 1, wherein a biologically active agent is incorporated into the adjunctive polymer system.

4. The wound dressing according to claim 1, wherein the fibrous wound dressing is biodegradable.

5. The wound dressing according to claim 3, wherein the biologically active agent is selected from the group consisting of antibiotics, analgesics, growth promoting agents, clotting agents, anesthetics, antiseptics, antioxidants, anti-inflammatories, and mixtures thereof.

6. The wound dressing according to claim 3, wherein the biologically active agent is contained within a controlled release component selected from the group consisting of a nanoparticle, cyclodextrin, microcapsule, micelle, liposome, fiber, bead, and combinations thereof.

7. The wound dressing according to claim 3, wherein the biologically active agent is a low water-solubility salt of the active agent, a complex of the active agent, a conjugate of the active agent, and combinations thereof.

8. The wound dressing according to claim 1, wherein the internal tissue or organ is selected from the group consisting of an artery, vein, liver and pancreas.

* * * * *